United States Patent [19]
Oehme et al.

[11] Patent Number: 5,886,217
[45] Date of Patent: Mar. 23, 1999

[54] METHOD OF PRODUCING ARYL-SUBSTITUTED, AMINO-ACYLATED PHOSPHONIC-ACID DERIVATIVES WITH THE AID OF METAL COMPLEXES OF CHIRAL, AMPHIPHILIC LIGANDS

[75] Inventors: Günther Oehme, Rostock; Ute Schmidt, Neu Roggentin; Silke Ziegler, Hamburg; Ingrid Grassert; Christine Fischer, both of Rostock, all of Germany

[73] Assignee: Degussa Aktiengesellschaft, Frankfurt, Germany

[21] Appl. No.: 974,802

[22] Filed: Nov. 20, 1997

[30] Foreign Application Priority Data

Nov. 20, 1996 [DE] Germany .................. 196 47 885.5
Jul. 17, 1997 [DE] Germany .................. 197 30 657.8

[51] Int. Cl.[6] .................................................. C07F 9/22
[52] U.S. Cl. ................... 562/15; 558/87; 562/15; 549/6; 549/218; 546/22
[58] Field of Search .................. 558/87; 562/15; 549/6, 218; 546/22

[56] References Cited

U.S. PATENT DOCUMENTS 5,321,153  6/1994  Talley ........................ 562/16

FOREIGN PATENT DOCUMENTS 195 19 983  11/1996  Germany .
196 17 941  10/1997  Germany .

OTHER PUBLICATIONS

Schmidt U et al., Catalytic stereoselective synthesis of .alpha.–amino phosphonic acid derivatives by asymmetric hydrogenation, Synthetic Communication, 1996, 777–81.

Oehme G. et al., Increase in activity and enantioselectivity in asymmetric hydrogenation reactions catalyzed by chiral rhodium (I) complexes as a consequence of the action of amphiphiles, Chemical Abstracts, Apr. 13, 1992, 939.

Yan Y Y et al., Aqueous–phase rhodium hydroformylation of dodecene–1 with surface–active water–soluble phosphine, Chemicals Abstracts, Jul. 15, 1996, 855.

*Primary Examiner*—Samuel Barts
*Attorney, Agent, or Firm*—Pillsbury Madison & Sutro LLP

[57] ABSTRACT

The invention is relates to a method of producing aryl-substituted, amino-acylated phosphonic-acid derivatives with the aid of metal complexes of chiral amphiphilic ligands in that according to the invention α-N-acyl-protected, β-substituted alkene phosphone derivatives are asymmetrically hydrogenated in the presence of a chiral rhodium catalyst in a solvent or a suspension. The use of the micelle-forming catalyst makes possible the hydrogenation of unsaturated phosphonic-acid derivatives in water with a high reaction rate with the obtainment of very good enantiomeric excesses.

16 Claims, No Drawings

METHOD OF PRODUCING ARYL-SUBSTITUTED, AMINO-ACYLATED PHOSPHONIC-ACID DERIVATIVES WITH THE AID OF METAL COMPLEXES OF CHIRAL, AMPHIPHILIC LIGANDS

This application is based on applications nos. 196 47 885.5 and 197 30 657.8 filed in Germany on Nov. 26, 1996 and Jul. 17, 1997, respectively, the content of which is incorporated hereinto by reference.

BACKGROUND OF THE INVENTION

1. Field of the Invention

The invention is related to a method of producing α-amino-acylated, aryl-substituted phosphonic-acid derivatives in optically active form with the aid of chiral, amphiphilic metal-complex catalysts by means of novel, micellar, asymmetric, catalytic hydrogenation of suitable precursors.

2. Prior Art

Methods for asymmetric, catalytic hydrogenation in the presence of amphiphilic metal-complex catalysts are known only for two-phase reactions.

Micelle-forming, chiral metal complexes are also known as catalysts in asymmetric hydrolysis reactions ((a) P. Scrimin, U. Tonellato, "Ligand Surfactants: Aggregation, Cations Binding and Transport, and Catalytic Properties" in Surfactants in Solution, vol. 11, editors K. L. Mittal and D. O. Shah, Plenum Press, New York, 1991; (b) P. Scrimin, P. Tecilla, U. Tonellato, J. Org. Chem. 1994, 59, 4194; (c) A. Bunton, P. Scrimin, P. Tecilla, J. Chem. Soc., Perkin Trans. 2 1996, 419; (d) J. Budka, F. Hampl, F. Liska, P. Scrimin, P. Tecilla, J. Mol. Cat. 1996, 104, L201).

Furthermore, a number of reactions catalyzed by chiral rhodium phosphane complexes in the presence of achiral detergents in water are known in which the formation of the micellar systems is brought about by the detergents added. Thus, in the hydrogenation of dehydroamino-acid derivatives enantioselectivities of up to 97% ee can be achieve ((a) G. Oehme, E. Paetzold, R. Selke, J. Mol. Catal. 1992, 71, L1; (b) I. Grassert, E. Paetzold, G. Oehme, Tetrahedron 1993, 49, 6605; (c) A. Kumar, G. Oehme, J. P. Roque, M. Schwarze, R. Selke, Angew. Chem. 1994, 106, 2272; (d) G. Oehme, I. Grassert, H. N. Flach, "Asymmetric Complex Catalysis in Micellar Systems" in Aqueous Organometallic Chemistry and Catalysis, editors I. T. Horváth, F. Joó, Kluwer Academic Publishers, Dordrecht, 1995, p. 245; (e) H. N. Flach, I. Grassert, G. Oehme, M. Capka, Colloid Polym. Sci. 1996, 274, 261).

It is also known that surface-active, chiral, sulfonated bisphosphanes can be used in the form of their rhodium complexes in water or water mixtures with organic solvents with moderate success with regard to the stereoselectivity and activity for the asymmetric hydrogenation of amino-acid precursors (H. Ding, B. E. Hanson, J. Bakos, Angew. Chem. 1995, 107, 1728).

It is furthermore known that chiral, α-amino-acylated phosphonic-acid derivatives can be produced by means of the asymmetric hydrogenation of appropriate dehydroprecursors in the presence of optically active rhodium-complex catalysts as well as analogous racemic compounds with known achiral catalysts, during which high reaction rates and selectivities ≧90% ee are achieved only in organic solvents (U. Schmidt, G. Oehme, H. W. Krause, Synth. Commun. 1996, 26, 777 and German patent application 195 19 983.9).

Thus, Schöllkopf et al. (U. Schöllkopf, I. Hoppe, A. Thiele, Liebigs Ann. Chem. 1985, 555–559) achieved optical yields of 76% ee by means of the hydrogenation of α-N-formyl-α, β-dehydrophosphonic-acid dimethyl esters with the known, optically active DIOP-Rh catalyst in the synthesis of AlaP. In another method (U.S. Pat. No. 5,321, 153) the Z-protected α-amino-α, β-dehydrophosphonic-acid esters are hydrogenated with a DIPAMP-Rh- complex catalyst to the saturated compounds with optical yields of approximately 90%.

The α-amino-acylated-α, β-unsaturated precursors necessary in all these instances are produced according to known synthesis routes ((a) U. Schöllkopf, I. Hoppe, A. Thiele, Liebigs Ann. Chem. 1985, 555–559; (b) V. S. Brovarets, K. V. Zyuz, L. N. Budnik, V. A. Solodenko, B. S. Dratsch, Zh. Obsch. Khim. 1993, 63, 1259; (c) U.S. Pat. No. 5,321,153).

In addition to racemate separations, various stoichiometric methods are known which all use optically active auxiliaries and likewise result in the production of optically active α-aminophosphonic acids ((review articles: (a) B. Dharwan, D. Redmore, Phosphorous, Sulfur and Silicon 1987, 32, 119; (b) V. P. Kukhar, V. A. Soloshonov, V. A. Solodenko, Phosphorus, Sulfur and Silicon 1994, 92, 239).

SUMMARY OF THE INVENTION

The invention addresses the problem of developing a catalytic hydrogenation method for producing chiral α-N-acylated aminophosphonic-acid derivatives which method comprises the novel catalyst type according to German patent application 196 17 941.6 and makes possible therewith high chemical and optical yields of target products using known, unsaturated phosphonic-acid derivatives while broadening the palette of solvents and avoiding the disadvantages of other methods.

According to the invention an α-N-acyl-protected, β-substituted alkene phosphonic-acid derivative of the general formula II

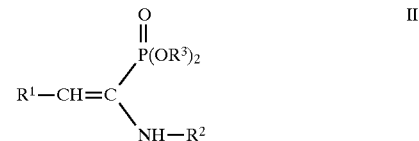

in which
R$^1$, R$^2$ and R$^3$ have the meanings indicated in general formula I is asymmetrically hydrogenated in the presence of a chiral rhodium catalyst of the general formula III

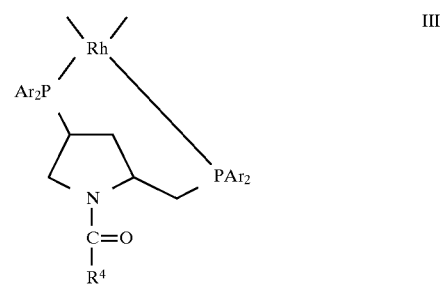

in which R$^4$=(OCH$_2$—CH$_2$)$_n$OC$_m$H$_{2m+1}$ and n≧4 and m≧8 and Ar=alkyl- or halogen-substituted phenyl groups, or as it was described in German Patent Application 196 17 941.6,in a solvent, preferably in water, or in a suspension at temperatures between −20° C. and +50° C. and at a hydrogen pressure between 0.1 and 10 MPa, especially preferably at 0.1 MPa hydrogen pressure, and with a catalyst/substrate ratio of 1:50 to 1:2000, preferably 1:100 to 500.

The free valences of the central atoms of the complex of general formula III are intended to indicate that ligands which are not determined in detail here are coordinated on the central atom. The exact ligand sphere during the hydrogenation is a function of the potentially available ligand molecules in the mixture but is in any case variable.

If the hydrogenation takes place at low temperatures, in particular an alcohol or mixtures of the like with water function as solvent; on the other hand, water is preferably used at +25° C. The aryl-substituted amino-acylated phosphonic-acid derivatives obtained in accordance with the invention have the general formula I

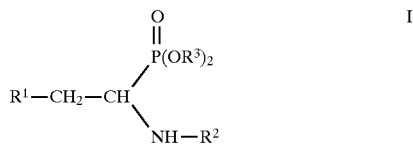

in which

R$^1$=phenyl, fluorophenyl such as 2-, 3- or 4-fluorophenyl, nitrophenyl such as 4-nitrophenyl, trifluoromethyl, alkylphenyl such as 4-methylphenyl, alkoxyphenyl such as 4-methoxyphenyl or dimethoxyphenyl, biphenyl, thienyl such as 2- or 3-thienyl, furyl such as 2- or 3-furyl, pyridyl such as 3- or 4-pyridyl, naphthyl such as 1- or 2-naphthyl and anthracenyl, R$^2$=formyl, acetyl, benzoyl, benzyloxycarbonyl (Cbz), tert.-butoxycarbonyl (BOC) and o-nitrobenzoyl and R$^3$=H, methyl, ethyl, propyl and isopropyl.

In order to produce the compounds of formula I in optically active form the prochiral precursors II are asymmetrically hydrogenated under the mild conditions indicated at a high rate and in high stereoselectivity by the chiral catalyst. The catalyst is produced by complex formation with suitable donor atoms by conversion with metal complexes. It is advantageous thereby to allow said process to take place in situ.

The principle of this method is based on the use of organized systems which are quite interesting on account of their supramolecular structures ((a) J. M. Lehn, Angew. Chem. 1988, 100, 91; (b) F. Vögtle, Supramolekulare Chemie, B. G. Teubner, Stuttgart, 1989) and on account of their use as mimetic substances for enzymatic catalyses: ((a) T. Kunitake, S. Shinkai, Adv. Phys. Org. Chem. 1980, 17, 435; (b) J. H. Fendler, Membrane Mimetic Chemistry, John Wiley & Sons, New York, 1982; (c) C. A. Bunton, G. Savelli, Adv. Phys. Org. Chem. 1986, 22, 213; (d) F. M. Menger, Angew. Chem. 1991, 103, 1104; (e) M. L. Carreto, S. Rubio, D. Pérez-Bendito, Analyst 1996, 121, 33R).

The invention is characterized in particular by the amphiphilic catalyst, which forms micelles in water which permit the course of hydrogenating reactions in water and extremely accelerate it compared to a non-amphiphilic catalyst in pure water and result in the hydrogenation of aryl-substituted, amino-acylated phosphonic-acid derivatives in excesses of enantiomers which become comparable to those in methanol as solvent. Thus, in a direct comparison of example 5 with examples 6 and 7 an extraordinary increase of activity from 720 min to 33 min and 55 min half-life (t/2) and an increase of enantioselectivity from 91% ee up to 94% ee can be determined with the novel ligands. The selectivity can be further elevated in accordance with the invention by the addition of further chiral or achiral amphiphilic substances (see examples 8 to 14) containing no metal complex in bound form; it is advantageous and almost optimal if 10 to 20 mol amphiphilic substance are added per mol catalyst; however, higher molar additives are also tolerated.

The target products produced according to the method of the invention have valuable pharmacological qualities which make it possible to use them as medicaments.

DETAILED DESCRIPTION OF PREFERRED EMBODIMENTS OF THE INVENTION

The invention is explained in a non-limiting manner with the following examples.

Examples of implementation

EXAMPLES 1 TO 4

Hydrogenation process: General formula in methanol

The hydrogenation of 0.5 mmol α-N-benzoylamino-β-phenylethylene phosphonic-acid dimethyl ester is carried out at 25° C. and 0.1 MPa hydrogen pressure in 7.5 ml methanol under the addition of 0.005 mmol [Rh(COD)$_2$]BF$_4$. In order to form the catalyst the phosphane and the rhodium complex are agitated in an oxygen-free hydrogenation vessel for 15 min. The hydrogenation is begun thereafter. The values for t/2 given in the following examples indicate the time for the absorption of half of the theoretical amount of hydrogen.

EXAMPLE 3

(S)-α-N-benzoylamino-β-phenylethyl phosphonic-acid dimethyl ester

After the hydrogenation (see general method in methanol) of α-N-benzoylamino-β-phenylethylene phosphonic-acid dimethyl ester (0.5 mmol) in 7.5 ml methanol in the presence of 0.005 mmol of the complex catalyst, produced from 0.005 mol [Rh(COD)$_2$]BF$_4$ and 1b (formula III R$^1$=O(CH$_2$CH$_2$O)$_{10}$C$_{12}$H$_{25}$) the solvent was drawn off in a vacuum and the residue dissolved in a little dichloromethane, put over a column filled with a 5 cm layer of silica gel, during which the rhodium complex is removed and the filtrate re-evaporated to low bulk. Dichloromethane/methanol=9/1 was used thereby as eluent. The yield is 95 to 99%. The enantiomeric excess is 97% ee and is determined by HPLC on a Chiracel OD column (Baker Chemicals company, Gross Gerau) on a 1090 liquid chromatograph, Hewlett-Packard. Melting point 115°–118° C., HPLC>99% 33, C$_{17}$H$_{20}$NO$_4$P (333.3 g/mol)

Calc. (%): C 61.25 H 6.05 N 4.20 P 9.29

Obs. (%): C 61.28 H 6.12 N 4.23 P 9.91

$[\alpha]_D^{23}$=101.9 (c=1.01, methanol). The configuration is (S).

$^{31}$P-NMR: δ27.1 ppm (CDCl$_3$).

EXAMPLES 5 TO 15

Hydrogenation process: General formula in water

The hydrogenation of 0.5 mmol α-N-benzoylamino-β-phenylethylene phosphonic-acid dimethyl ester is carried out at 25° C. and 0.1 MPa hydrogen pressure in 7.5 ml water under the addition of 0.005 mmol [Rh(COD)$_2$]BF$_4$. In order to form the catalyst the amphiphilic phosphane, the rhodium complex (and the additional amphiphilic substance) are agitated in an oxygen-free hydrogenation vessel for 15 min. The hydrogenation is begun thereafter. The values for t/2 given in the following examples indicate the time for the absorption of half of the theoretical amount of hydrogen.

EXAMPLE 8

(S)-α-N-benzoylamino-β-phenylethyl phosphonic-acid dimethyl ester

After the end of the hydrogenation of α-N-benzoylamino-β-phenylethylene phosphonic-acid dimethyl ester (0.5 mmol) in 7.5 ml water in the presence of 0.005 mmol of the complex catalyst produced from 0.005 mol [Rh(COD)$_2$]BF$_4$ and 1b (formula III R$^1$=O(CH$_2$CH$_2$O)$_{10}$C$_{12}$H$_{25}$) and 0.1 mmol SDS the mixture is extracted with chloroform and separated from the aqueous phase. The chloroform is removed in a vacuum and the residue is dissolved in a little dichloromethane put over a column filled with a 5 cm layer of silica gel, during which the rhodium complex is removed and the filtrate re-evaporated to low bulk. Dichloromethane/methanol=9/1 was used thereby as eluent. The yield is 60 to 70%. The enantiomeric excess is 98% ee and is determined by HPLC on a Chiracel OD column (Baker Chemicals company, Gross Gerau) on a 1090 liquid chromatograph, Hewlett-Packard.

Melting point 115°–118° C., HPLC>99% 33, C$_{17}$H$_{20}$NO$_4$P (333.3 g/mol)
Calc. (%): C 61.25 H 6.05 N 4.20 P 9.29
Obs. (%): C 61.47 H 6.06 N 4.03 P 9.38
[α]$_D^{23}$=107.2 (c=1.01, methanol). The configuration is (S).
$^{31}$P-NMR: δ27.1 ppm (CDCl$_3$).

The examples are summarized in a table and were carried out analogously to the formulas indicated above.

Substrate: α-N-benzoylamino-β-phenylethylene phosphonic-acid dimethyl ester (0.5 mmol) in 7.5 ml solvent with the aid of 0.005 mmol catalyst

| Example | Solvent | Ligand | Additional amphiphilic substance (mmol) | t/2 min | ee % Conf. (S) |
|---|---|---|---|---|---|
| 1 | MeOH | BPPM | — | 6 | 96 |
| 2 | MeOH | 1a | — | 6 | 98 |
| 3 | MeOH | 1b | — | 8 | 97 |
| 4 | MeOH | 1c | — | 4 | 97 |
| 5 | H$_2$O | BPPM | — | 720 Rh↓ | 91 |
| 6 | H$_2$O | 16 | — | 33 | 93 |
| 7 | H$_2$O | 1c | — | 55 | 95 |
| 8 | H$_2$O | 1b | SDS (0.2) | 4 | 98 |
| 9 | H$_2$O | 1b | SDS (0.1) | 8 | 97 |
| 10 | H$_2$O | 1b | SDS (0.05) | 10 | 97 |
| 11 | H$_2$O | 1b | SDS (0.02) | 16 | 96 |
| 12 | H$_2$O | 1b | SDS (0.01) | 19 | 95 |
| 13 | H$_2$O | 1b | CTAHSO$_4$ (0.2) | 11 | 98 |
| 14 | H$_2$O | 1b | Tween 40 (0.01) | 12 | 96 |
| 15 | H$_2$O | 1c | SDS (0.2) | 6 | 98 |

BPPM: N-t-butyloxycarbonyl-4-diphenylphosphino-2-diphenylphosphinomethyl pyrrolidine
SDS: Sodium docecylsulfate Ligands 1a, 1b and 1c correspond to the following formula:

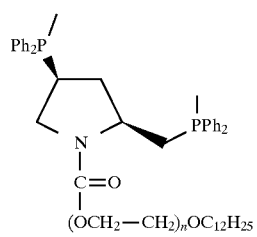

1a n = 4   1b n = 10   1c n = 23

What is claimed is:

1. A method of producing optically active, aryl-substituted phosphonic-acid derivatives of the general formula I

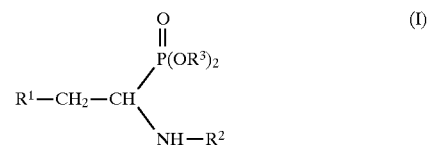

with the aid of metal complexes of chiral, amphiphilic ligands, wherein α-N-acyl-protected, β-substituted alkene phosphonic acids of the general formula II

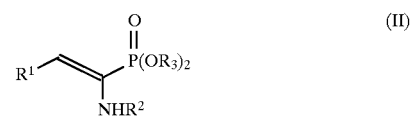

in which
R$^1$ is a member selected from the group consisting of phenyl, fluorophenyl, nitrophenyl, trifluoromethyl, alkylphenyl, alkoxyphenyl, biphenyl, thienyl, furyl, pyridyl, naphthyl and anthracenyl,
R$^2$ is a member selected from the group consisting of formyl, acetyl, benzoyl, benzyloxycarbonyl (Cbz), tert-butoxycarbonyl (BOC) and o-nitrobenzoyl and
R$^3$ is a member selected from the group consisting of H, methyl, ethyl, propyl and isopropyl are hydrogenated to compounds of the general formula I in the presence of a chiral rhodium catalyst of the general formula III

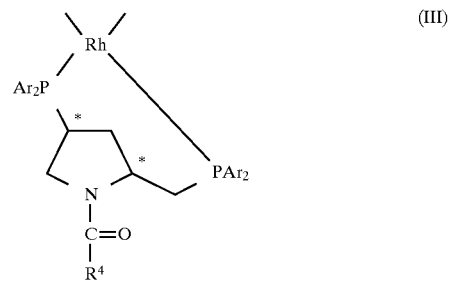

in which
R$^4$ is (OCH$_2$-CH$_2$)$_n$OC$_m$H$_{2m+1}$, wherein n≧4 and m≧8 and
Ar is alkyl- or halogen-substituted phenyl groups.

2. The method of claim 1, wherein said fluorophenyl is 2-, 3- or 4-fluorophenyl.

3. The method of claim 1, wherein said nitorphenyl is 4-nitorphenyl.

4. The method of claim 1, wherein said alkylphenyl is 4-methylphenyl.

5. The method of claim 1, wherein said alkoxyphenyl is 4-methoxyphenyl or dimethoxyphenyl.

6. The method of claim 1, wherein said thienyl is 2- or 3-thienyl.

7. The method of claim 1, wherein said furyl is 2- or 3-furyl.

8. The method of claim 1, wherein said pyridyl is 3- or 4-pyridyl.

9. The method of claim 1, wherein said naphthyl is 1-or 2-naphthyl.

10. The method according to claim 1, wherein the hydrogenation takes place in water or water-alcohol mixtures or in an alcohol.

11. The method according to claim 10, wherein the alcohol is methanol.

12. The method according to claim 1, wherein the hydrogenation is carried out at temperatures of −20° C. to +50° C.

13. The method according to claim 1, wherein the hydrogenation is carried out at a hydrogen pressure between 0.1 and 10 MPa.

14. The method according to claim 1, wherein the catalyst/substrate ratio is between 1:50 and 1:2000.

15. The method according to claim 13, wherein the hydrogenation is carried out at a hydrogen pressure of 0.1 MPa.

16. The method according to claim 14, wherein the catalyst/substrate ratio is between 1:100 and 1:500.

* * * * *